US011806202B2

(12) United States Patent
Kadobayashi et al.

(10) Patent No.: US 11,806,202 B2
(45) Date of Patent: Nov. 7, 2023

(54) MILL BLANK FOR DENTAL CAD/CAM WITH CUTOUT PORTION FOR POSITIONING

(71) Applicant: SHOFU INC., Kyoto (JP)

(72) Inventors: Yusei Kadobayashi, Kyoto (JP); Masako Shigezawa, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/679,291

(22) Filed: Aug. 17, 2017

(65) Prior Publication Data

US 2018/0055612 A1 Mar. 1, 2018

(30) Foreign Application Priority Data

Aug. 17, 2016 (JP) ................................. 2016-160255

(51) Int. Cl.
*A61C 13/00* (2006.01)
*A61K 6/17* (2020.01)
*A61K 6/802* (2020.01)

(52) U.S. Cl.
CPC ...... *A61C 13/0022* (2013.01); *A61C 13/0004* (2013.01); *A61K 6/17* (2020.01); *A61K 6/802* (2020.01); *Y10T 428/12229* (2015.01)

(58) Field of Classification Search
CPC ............ A61C 13/0022; A61C 13/0004; A61K 6/0008; A61K 6/0205; A61K 6/17; A61K 6/802; Y10T 428/12229
See application file for complete search history.

(56) References Cited

U.S. PATENT DOCUMENTS

| 2003/0125189 A1 | 7/2003 | Castro et al. |
| 2007/0275352 A1 | 11/2007 | Gubler et al. |
| 2010/0028836 A1 | 2/2010 | Gubler et al. |

(Continued)

FOREIGN PATENT DOCUMENTS

| DE | 10 2006 023 673 | 11/2007 |
| DE | 10 2011 055 393 | 5/2013 |

(Continued)

OTHER PUBLICATIONS

Machine translation of DE 10 2011 055393. (Year: 2013).*

(Continued)

*Primary Examiner* — Patricia L. Nordmeyer
(74) *Attorney, Agent, or Firm* — WENDEROTH, LIND & PONACK, L.L.P.

(57) ABSTRACT

A mill blank for dental CAD/CAM for preparing a dental restoration by being installed in a CAD/CAM device, wherein, the mill blank for dental CAD/CAM has a columnar shape, has at least two recesses which includes a first recess opening to an upper surface of the mill blank and a second recess opening to a bottom surface of the mill blank and at least one notched portion in a circumference portion, the first recess and the second recess respectively include a first surface which is parallel to the upper surface and the bottom surface and a second surface which is a circumferential face concentric with the circumferential face of the mill blank and is vertical to the first surface, and the notched portion is composed of a surface parallel to the center axis of the columnar shape of the mill blank and contacts with the second surface.

12 Claims, 5 Drawing Sheets

(56) References Cited

U.S. PATENT DOCUMENTS

| | | | | |
|---|---|---|---|---|
| 2013/0221554 A1* | 8/2013 | Jung | ................ | B32B 18/00 264/16 |
| 2014/0377718 A1* | 12/2014 | Korten | ............... | A61C 13/0022 433/218 |
| 2016/0317258 A1* | 11/2016 | Steger | ................ | A61C 13/0022 |
| 2016/0338806 A1* | 11/2016 | Nazzal | ............... | A61C 13/0022 |
| 2017/0319304 A1* | 11/2017 | Borowski | .......... | A61C 13/0006 |

FOREIGN PATENT DOCUMENTS

| | | |
|---|---|---|
| EP | 2 384 718 | 11/2011 |
| JP | 10-328988 | 12/1998 |
| JP | 2005-514305 | 5/2005 |
| JP | 2006-521842 | 9/2006 |
| JP | 2012-5874 | 1/2012 |
| WO | 2013/072287 | 5/2013 |
| WO | 2013/117540 | 8/2013 |

OTHER PUBLICATIONS

Office Action dated Oct. 3, 2016, in corresponding Japanese Application No. 2016-160255, with English translation.
Office Action dated Jan. 30, 2017, in corresponding Japanese Application No. 2016-160255, with English translation.
Extended European Search Report dated Jan. 2, 2018, in corresponding European Application No. 17186600.7.
Office Action dated Aug. 30, 2019, in corresponding European Application No. 17186600.7.

* cited by examiner

MILL BLANK FOR DENTAL CAD/CAM WITH CUTOUT PORTION FOR POSITIONING

CROSS-REFERENCE TO RELATED APPLICATIONS

This application is based on and claims the benefit of priority from Japanese Patent Application Serial No. 2016-160255 (filed on Aug. 17, 2016), the contents of which are hereby incorporated by reference in their entirety.

BACKGROUND OF THE INVENTION

Field of the Invention

The present disclosure relates to a mill blank for dental CAD/CAM used for preparing a dental restoration and specifically, to a mill blank for dental CAD/CAM having a columnar disk shape.

Description of the Related Art

In the dental field, it has been known that a dental restoration is prepared by cutting a mill blank by using a CAD/CAM technique. In recent years, a plurality of dental restorations have been prepared by cutting one mill blank by using this CAD/CAM technique.

Further, a dental restoration may have been prepared from a remaining portion of a mill blank after cutting out other dental restoration. On CAD software, it is possible that a dental restoration is designed in a mill blank so as to avoid a portion from which other dental restoration was cut out in order to further cut and process (machine) the dental restoration from a remaining portion of the mill blank after cutting out other dental restoration. However, when the mill blank which is already cut and machined is installed in a CAD/CAM device, the directivity in the circumferential direction of the mill blank cannot be recognized. Therefore, the conventional mill blank cannot be easily installed so as to further cut and machine a dental restoration from a remaining portion of the mill blank after cutting out other dental restoration.

Japanese Unexamined Patent Application Publication No. 2012-5874 (JP 2012-5874 A) discloses a mill blank which has a columnar shape and is provided with a circumference groove.

However, when this conventional mill blank is installed in a CAD/CAM device, the directivity in the circumferential direction of the mill blank cannot be recognized. Therefore, the conventional mill blank cannot be easily installed so as to further cut and machine a dental restoration from a remaining portion of the mill blank after cutting out other dental restoration.

SUMMARY OF THE INVENTION

Technical Problem

In the conventional mill blank, when the mill blank is installed in a CAD/CAM device, the directivity in the circumferential direction of the mill blank cannot be recognized. Therefore, the conventional mill blank cannot be easily installed so as to further cut and machine a dental restoration from a remaining portion of the mill blank after cutting out other dental restoration.

Specifically, a data for cutting and machining is prepared by CAD in order to perform cutting and machining, and CAM performs cutting and machining a mill blank for dental CAD/CAM.

There are cases that other dental restoration is cut out from only a part of a mill blank for dental CAD/CAM, and then a dental restoration is cut out from the remaining portion of the mill blank for dental CAD/CAM.

In this case, a first cutting data in which other dental restoration is cut out from only a part of a mill blank for dental CAD/CAM is firstly prepared and a mill blank for dental CAD/CAM is cut based on the first cutting data.

Thereafter, a data for cutting out a (new) dental restoration is added to the first cutting data so as not to overlap other dental restoration in the first cutting data to prepare a second cutting data in which the dental restoration is cut out from the remaining portion, which is not cut in the first cutting out, of the mill blank for dental CAD/CAM. The mill blank for dental CAD/CAM is further cut based on the second cutting data.

However, in the conventional mill blank for dental CAD/CAM, when the mill blank for dental CAD/CAM is installed in a CAD/CAM device, it is difficult to install the mill blank for dental CAD/CAM at the same position and the same direction in the circumference direction as the position and the direction in the circumference direction in the first cutting out in which other dental restoration is cut out from only a part of the mill blank for dental CAD/CAM. Therefore, it was impossible to add a data for cutting out a dental restoration to the first cutting data so as to position the data for cutting out the dental restoration in a proximity position proximate to the data of other dental restoration in the first cutting data.

An object of the present invention is to provide a mill blank which may be easily installed so as to further cut and machine a dental restoration from a remaining portion of the mill blank after cutting out other dental restoration to solve the above described problem.

Solution to Problem

The present disclosure provides a mill blank for dental CAD/CAM for preparing a dental restoration by being installed in a CAD/CAM device, wherein, the mill blank for dental CAD/CAM has a columnar shape, the mill blank for dental CAD/CAM has at least two recesses which includes a first recess opening to an upper surface of the mill blank for dental CAD/CAM and a second recess opening to a bottom surface of the mill blank for dental CAD/CAM and at least one notched portion in a circumference portion, the first recess and the second recess respectively include a first surface which is parallel to the upper surface and the bottom surface and a second surface which is a circumferential face concentric with the circumferential face of the mill blank for dental CAD/CAM and is vertical to the first surface, and the notched portion is composed of a surface who and contacts with the second surface.

In the present disclosure, it is preferable that a diameter of the columnar shape of the mill blank for dental CAD/CAM is within a range of 95 to 100 mm, and a height of the columnar shape of the mill blank for dental CAD/CAM is within a range of 10 to 35 mm. In this case, it is preferable that a distance between the first recess and the second recess in the axial direction of the columnar shape of the mill blank for dental CAD/CAM is within a range of 9 to 11 mm. Further, in this case, it is preferable that a dimension from the center axis of the columnar shape of the mill blank for dental CAD/CAM to the first recess and the second recess is within a range of 90 to 98 mm.

In the present disclosure, it is preferable that the diameter of the columnar shape of the mill blank for dental CAD/CAM is 98 mm, and the height of the columnar shape of the mill blank for dental CAD/CAM is 14, 18 or 26 mm. In this case, it is preferable that a distance between the first recess and the second recess in the axial direction of the columnar shape of the mill blank for dental CAD/CAM is 10 mm. Further, in this case, it is preferable that a dimension from the center axis of the columnar shape of the mill blank for dental CAD/CAM to the first recess and the second recess is 94 mm.

In the present disclosure, it is preferable that the notched portion is composed of a plane surface or a curved surface parallel to the center axis of the columnar shape of the mill blank for dental CAD/CAM.

In the present disclosure, it is preferable that the mill blank for dental CAD/CAM has two recesses and one notched portion.

In the present disclosure, it is preferable that the mill blank for dental CAD/CAM consists of a ceramic material which is unsintered or is not subjected to final sintering. In this case, it is preferable that the ceramic material contains alumina or zirconia at a ratio of 95 wt. % or more. Further, in this case, it is preferable that a primary average particle diameter of the ceramic material is within the range of 0.01 to 10 µm.

The present disclosure provides a set including the mill blank for dental CAD/CAM of claim 1 and a holding portion of CAM which cut the mill blank for dental CAD/CAM, wherein, the holding portion includes an engaging portion which engages to a whole or the recess of the mill blank for dental CAD/CAM, the mill blank for dental CAD/CAM is hold at the engaging portion, and the holding portion further includes a positioning portion which fits in the notched portion of the mill blank for dental CAD/CAM.

Advantageous Effects of Invention

According to the present disclosure, the position and the direction in the circumference direction of a mill blank for dental CAD/CAM may be recognized. Therefore, when the mill blank for dental CAD/CAM is installed to a CAM device, the directivity in the circumferential direction of the mill blank may be recognized. As a result, the mill blank for dental CAD/CAM of the present disclosure may be always installed at a constant position or a constant direction in the circumference direction. Therefore, the mill blank for dental CAD/CAM of the present disclosure may be easily installed so as to further cut and machine a dental restoration from a remaining portion of the mill blank for dental CAD/CAM after cutting out other dental restoration.

In the case that a first cutting data in which other dental restoration is cut out from only a part of a mill blank for dental CAD/CAM is firstly prepared and a data for cutting out a (new) dental restoration is added to the first cutting data so as not to overlap other dental restoration in the first cutting data, the mill blank for dental CAD/CAM of the present disclosure may be always installed to a CAM device at a constant position or a constant direction in the circumference direction. Therefore, even if a data for cutting out a (new) dental restoration is added to the first cutting data so as to position the data for cutting out a (new) dental restoration in a proximity position proximate to the data of other dental restoration in the first cutting data, it may be prevented that a (new) restoration is cut out from the portion in which the dental restoration was cut out in the first cutting out.

Thus, in the mill blank for dental CAD/CAM of the present disclosure, when cutting out of a dental restoration from a mill blank for dental CAD/CAM is repeatedly performed, it is possible to prepare larger quantity of dental restorations than before.

DETAILED DESCRIPTION OF THE PREFERRED EMBODIMENTS

Now a specific description of the present disclosure is given.

A mill blank for dental CAD/CAM of the present disclosure is a molded body for cutting out a dental restoration by using a CAD/CAM technique. The mill blank for dental CAD/CAM of the present disclosure may be prepared by pressing a material provided into a mold, and curing or temporary calcining by heating the pressed material. The mill blank for dental CAD/CAM of the present disclosure has a columnar shape and may have, for example, a diameter of the columnar shape within a range of 95 to 100 mm, and a height of the columnar shape within a range of 10 to 35 mm. It is preferable that the diameter of the columnar shape is 98 mm and the height of the columnar shape is 14, 18 or 26 mm. It is preferable that an upper surface and a bottom surface of the mill blank for dental CAD/CAM is parallel each other and a side surface of the mill blank for dental CAD/CAM is vertical to the upper surface and the bottom surface.

A material of the mill blank for dental CAD/CAM of the present disclosure is not limited particular, and any materials such as a resin material, an inorganic material, and a composite material may be used as the material of the mill blank for dental CAD/CAM of the present disclosure. Preferable resin materials include an acrylic resin material, preferable inorganic materials include ceramic material such as an aluminosilicate glass, zirconia and alumina, and preferable composite materials include a mixed material of an acrylic resin material and an inorganic powder.

More preferable materials of the mill blank for dental CAD/CAM of the present disclosure include a ceramic material which is unsintered or is not subjected to final sintering. In this case, it is preferable that the ceramic material contains alumina or zirconia at a ratio of 95 wt. % or more. Further, it is preferable that the primary average particle diameter of the ceramic material is within a range of 0.01 to 10 μm, in this case.

The mill blank for dental CAD/CAM of the present disclosure may have a single layer structure having single color. Further, the mill blank for dental CAD/CAM of the present disclosure may be prepared by molding a plurality of stacked layers having different colors from each other. In this case, the mill blank for dental CAD/CAM may have 2 to 8 layers. Among them, it is preferable that the mill blank for dental CAD/CAM has at least three layers including an enamel color layer, a dentin color layer and a cervical area color layer.

In the present disclosure, a dental restoration includes a dental prosthesis and an artifact used for a dental prosthesis and examples of the dental restoration include an inlay, a crown, a bridge and an artificial tooth.

The mill blank for dental CAD/CAM of the present disclosure has at least two recesses in a circumference portion of the columnar shape. Specifically, the mill blank for dental CAD/CAM of the present disclosure has at least two recesses which includes a first recess opening to an upper surface of the mill blank for dental CAD/CAM and a second recess opening to a bottom surface of the mill blank for dental CAD/CAM. Thus, the first recess is provided on a transition portion of the upper surface and the second recess is provided on a transition portion of the bottom surface and the side surface. The mill blank for dental CAD/CAM of the present disclosure may have other recess other than the at least two recesses.

The first recess and the second recess respectively include a first surface which is parallel to the upper surface and the bottom surface and a second surface which is a circumferential surface concentric with the circumferential surface of the mill blank for dental CAD/CAM and is vertical to the first surface.

The second surface contacts with the upper surface or the bottom surface of the mill blank for dental CAD/CAM and does not contact with the side surface of the mill blank for dental CAD/CAM. The first surface contacts with the side surface of the mill blank for dental CAD/CAM and does not contact with the upper surface and the bottom surface of the mill blank for dental CAD/CAM.

The first surface is visible from an upper surface side and a bottom surface side of the columnar shape of the mill blank for dental CAD/CAM and has a planar ring shape. The first surface engages to a holding portion of CAM to fix the mill blank for dental CAD/CAM to CAM. Because the first surface is composed of a plane surface, the first surface may easily engage to the holding portion of CAM. Therefore, the first surface may stably engage to the holding portion of CAM.

The second surface is visible from a side surface side of the columnar shape of the mill blank for dental CAD/CAM and is a circumferential surface concentric with the circumferential surface of the mill blank for dental CAD/CAM. The second surface engages to the holding portion of CAM to fix the mill blank for dental CAD/CAM to CAM. Because the second surface is composed of a curved surface, the second surface may easily engage to the holding portion of CAM. Therefore, the second surface may stably engage to the holding portion of CAM.

In preferable embodiment, for example, the first recess and the second recess may be formed so that a distance between the first recess and the second recess in the axial direction of the columnar shape of the mill blank for dental CAD/CAM is within a range of 9 to 11 mm. Further, the first recess and the second recess may be formed so that a dimension from the center axis of the columnar shape of the mill blank for dental CAD/CAM to the first recess and the second recess is within a range of 90 to 98 mm, in preferable embodiment. In more preferable embodiment, for example, the first recess and the second recess may be formed so that the distance between the first recess and the second recess in the axial direction of the columnar shape of the mill blank for dental CAD/CAM is 10 mm. Further, the first recess and the second recess may be formed so that the dimension from the center axis of the columnar shape of the mill blank for dental CAD/CAM to the first recess and the second recess is 94 mm.

The mill blank for dental CAD/CAM of the present disclosure has at least one notched portion in the circumference portion of the columnar shape. The notched portion is composed of a surface parallel to the center axis of the columnar shape of the mill blank for dental CAD/CAM. When the notched portion is not composed of a surface parallel to the center axis of the columnar shape of the mill blank for dental CAD/CAM, it is impossible to stably install the mill blank for dental CAD/CAM to CAM. Further, cutting may not be accurately performed. In addition, cracking and falling off may be caused.

Further, the notched portion contacts with the second surface. In the present disclosure, "the notched portion contacts with the second surface" means the contact of a surface which constitutes the notched portion and the second surface of the recess when the surface which constitutes the notched portion and the second surface of the recess are projected to the upper surface direction or the bottom surface direction.

When the notched portion is formed over the second surface in the direction toward the center axis of the mill blank for dental CAD/CAM, the notched portion may overlap with an area in which a dental restoration is cut and machined. Therefore, the dental restoration which is cut out may not have desirable shape. Further, when the notched portion does not contact with the second surface, the mill blank for dental CAD/CAM may be not sufficiently connected to CAM device. Therefore, it may be impossible to stably install the mill blank for dental CAD/CAM to CAM.

The surface which constitutes the notched portion may be, for example, a plane surface or a curved surface parallel to the center axis of the columnar shape of the mill blank for dental CAD/CAM. The surface which constitutes the notched portion is preferably a curved surface and is more preferably a circular arc surface. More specifically, a portion which contacts with the second surface of the recess is a circular arc surface. In the case that the surface which constitutes the notched portion is a circular arc surface, it is preferable that the center of the circle including an arc of the circular arc surface is not within the mill blank for dental CADCAM when the surface which constitutes the notched portion and the second surface of the recess are is projected to the upper surface direction or the bottom surface direction.

When the notched portion is composed of only plane surface, a portion which is not recessed and positioned in the center of the height direction of the columnar shape of the mill blank for dental CAD/CAM (a portion which is sandwiched between the first recess and the second recess) is significantly cut. That is, a portion to be held by CAM is significantly lost to decrease a holding force. Therefore, a breakage such as a cracking and a chipping and falling off from the holding portion may become easily occur. The curved surface of the notched portion is preferably a circular arc surface of a circle having a diameter within a range of 1 to 50 mm, more preferably within a range of 5 to 20 mm.

The notched portion may be formed only on a portion which is sandwiched between the first recess and the second recess. Alternatively, the notched portion may be formed by cutting the mill blank for dental CAD/CAM by a surface parallel to the center axis of the columnar shape of the mill blank for dental CAD/CAM from the bottom surface to the upper surface.

CAM in the present disclosure cuts the mill blank for dental CAD/CAM of the present disclosure and has a holding portion which holds the mill blank for dental CAD/CAM over the whole of the circumference without the notched portion. By holding the mill blank for dental CAD/CAM over the substantially whole of the circumference, it may be prevented that a breakage such as cracking and chipping and falling off from the holding portion of the mill blank for dental CAD/CAM occurs.

The holding portion of CAM may have, for example, a cylindrical shape which may holds the recess of the mill blank for dental CAD/CAM. The mill blank for dental CAD/CAM may be held by nipping with two cylindrical members which constitute the holding portion. Alternatively, the mill blank for dental CAD/CAM may be held by nipping with two half cylindrical members formed with grooves which may hold the recess of the mill blank for dental CAD/CAM.

The holding portion of CAM may be provided with an engaging portion which engages to the notched portion provided on the mill blank for dental CAD/CAM. In this case, the mill blank for dental CAD/CAM may be positioned in the circumference direction by engaging this engaging portion with the notched portion. It is preferable that the engaging portion has a shape which may be fitted to the notched portion provided on the mill blank for dental CAD/CAM. However, it is not necessary that the shape of the notched portion always match with the shape of the holding portion which is fitted to the notched portion.

When the notched portion is composed of the plane surface, it is preferable that a portion of the holding portion of CAM is projected in planar shape. Further, when the notched portion is composed of the circular arc surface, it is preferable that a portion of the holding portion of CAM is projected in circular arc surface shape.

Next, a specific description is given with reference to the drawings.

Figure 1A:
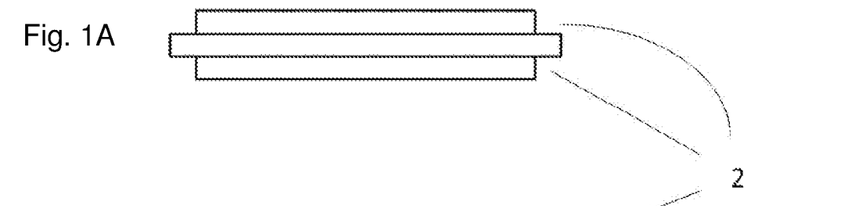
FIG. 1(A) is a side view of a conventional mill blank for dental CAD/CAM (disk).
Figure 1B:
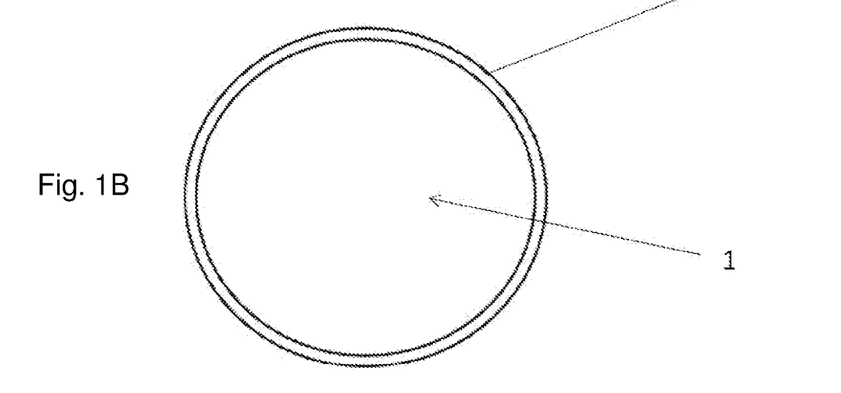
FIG. 1(B) is a plane view of a conventional mill blank for dental CAD/CAM (disk).

FIGS. 1(A) and (B) respectively show a side view and a plane view of a conventional mill blank for dental CAD/CAM (disk) 1. The conventional mill blank for dental CAD/CAM has only recesses 2 which are formed over the whole of the circumference portion and does not have a notched portion. Therefore, because the conventional mill blank for dental CAD/CAM has a uniform shape in the circumference direction with the center of gravity of the mill blank for dental CAD/CAM as a center as seen from a plane view of the mill blank for dental CAD/CAM (that is, has a uniform shape in a rotation direction with the center axis of the columnar shape of the mill blank for dental CAD/CAM), it is impossible to identify the direction of the mill blank for dental CAD/CAM in the circumference direction. Thus, when the mill blank for dental CAD/CAM is installed to a holding portion of CAM, there are cases when the mill blank for dental CAD/CAM is installed in a wrong direction in the circumference direction because the mill blank for dental CAD/CAM rotates in the circumference direction. As a result, it is impossible to always install the conventional mill blank for dental CAD/CAM at a constant position or a constant direction in the circumference direction.

Figures 2A, 2B:
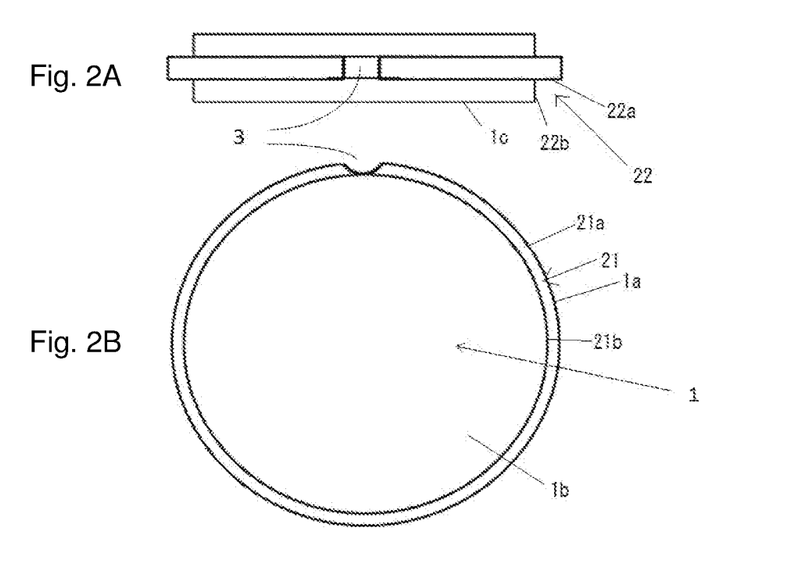
FIG. 2(A) is a side view of a mill blank for dental CAD/CAM of one embodiment of the present disclosure.
FIG. 2(B) is a plane view of a mill blank for dental CAD/CAM 1 of one embodiment of the present disclosure.

FIGS. 2(A) and (B) respectively show a side view and a plane view of a mill blank for dental CAD/CAM (disk) 1 of one embodiment of the present disclosure. The mill blank for dental CAD/CAM 1 of the present embodiment has a notched portion 3 on a circumference portion 1a in addition to recesses 2 as compared with the conventional mill blank for dental CAD/CAM shown in FIG. 1. More specifically, the mill blank for dental CAD/CAM 1 of the present embodiment has a first recess 21 which opens to an upper surface 1b of the mill blank for dental CAD/CAM 1, a second recess 22 which opens to a bottom surface 1c of the mill blank for dental CAD/CAM 1, and the notched portion 3. The first recess 21 includes a first surface 21a which is parallel to the upper surface 1b of the mill blank for dental CAD/CAM 1 and a second surface 21b which is a circumferential face concentric with the circumferential surface of the mill blank for dental CAD/CAM 1 and is vertical to the first surface 21a. The second recess 22 includes a first surface 22a which is parallel to the bottom surface 1c of the mill blank for dental CAD/CAM 1 and a second surface 22b which is a circumferential surface concentric with the circumferential surface of the mill blank for dental CAD/CAM 1 and is vertical to the first surface 22a. In the present disclosure, a part of the recesses 2 is notched by the notched portion 3. Therefore, it is understood that the recesses 2 do not extend over the whole of the circumference portion of the mill blank for dental CAD/CAM 1. As shown in FIG. 2(B), the notched portion 3 surface-contacts with the second surface 21b of the first recess 21 (and the second surface 22b of the second recess 22).

Because the mill blank for dental CAD/CAM 1 of the present embodiment has the notched portion 3, the direction of the mill blank for dental CAD/CAM in the circumference direction may be identified. Therefore, when the mill blank for dental CAD/CAM is installed on a holding portion of CAM, there are no cases when the mill blank for dental CAD/CAM is installed in a wrong direction in the circumference direction by rotation of the mill blank for dental CAD/CAM in the circumference direction. As a result, the mill blank for dental CAD/CAM of the present embodiment may be always installed at a constant position or a constant direction in the circumference direction.

In the present embodiment, the notched portion 3 is composed of a circular arc surface parallel to the center axis of the columnar shape of the mill blank for dental CAD/CAM 1. Further, the center of a circle including an arc of the circular arc surface is positioned on outside of the mill blank for dental CAD/CAM.

Figure 3A:
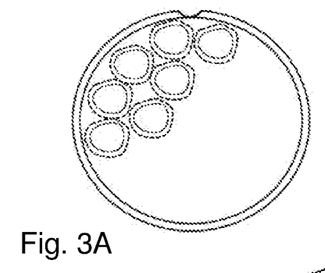
FIG. 3(A) is a schematic view of the mill blank for dental CAD/CAM of one embodiment in a state that the mill blank for dental CAD/CAM is removed from the holding portion of CAM after first cutting out a dental restoration based on a cutting data.
Figure 3B:
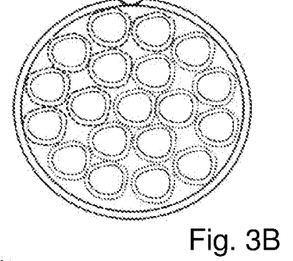
FIG. 3(B) is a schematic view of the mill blank for dental CAD/CAM of one embodiment in a state that the mill blank for dental CAD/CAM is removed from the holding portion of CAM after second cutting out a dental restoration based on a cutting data after the first cutting out.
Figure 3C:
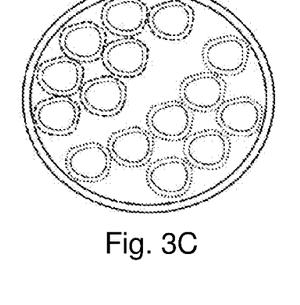
FIG. 3(C) shows a schematic view of the conventional mill blank for dental CAD/CAM after second cutting out which does not use the mill blank for dental CAD/CAM of the present disclosure.

FIG. 3(A) shows a schematic view of the mill blank for dental CAD/CAM of the present embodiment in a state that the mill blank for dental CAD/CAM is removed from the holding portion of CAM after first cutting out a dental restoration based on a cutting data. FIG. 3(B) shows a schematic view of the mill blank for dental CAD/CAM of the present embodiment in a state that the mill blank for dental CAD/CAM is removed from the holding portion of CAM after second cutting out a dental restoration based on a cutting data after the first cutting out. FIG. 3(C) shows a schematic view of the conventional mill blank for dental CAD/CAM after second cutting out. In FIG. 3(C), the mill blank for dental CAD/CAM of the present disclosure is not used. An arrangement shown in FIG. 3 is the same as the arrangement in a cutting data used for cutting out a dental restoration from a mill blank for dental CAD/CAM.

In FIGS. 3(a) to (C), a form of the dental restoration to be prepared is shown by aggregated solid lines and an actually cut area is shown by broken lines. Further, the thickness of the solid lines which show a form of the dental restoration to be prepared by first cutting out is larger than the thickness of the solid lines which show a form of the dental restoration to be prepared by second cutting out. Similarly, the thickness of the broken lines which show an actually cut area by first cutting out is larger than the thickness of the broken lines which show an actually cut area by second cutting out.

In the mill blank for dental CAD/CAM after the first cutting out a dental restoration show in FIG. 3(A), other dental restoration may be further cut out from a remaining portion of the mill blank for dental CAD/CAM in which the dental restoration is not cut out in first cutting out. When other dental restoration is further cut out from the remaining portion of the mill blank for dental CAD/CAM (that is, the second cutting out a dental restoration is performed), it is required to re-install the mill blank for dental CAD/CAM to the holding portion of CAM.

That is, it is impossible to further cut out the dental restoration from a portion in which other dental restoration was cut out in the first cutting out. Therefore, a portion capable of cutting out a dental restoration is calculated by the cutting data for the first cutting out a dental restoration to prepare a cutting data for the second cutting out a dental restoration.

On this point, in the present embodiment, it becomes possible to install the mill blank for dental CAD/CAM to the holding portion of CAM in the second cutting out of the mill blank for dental CAD/CAM at the position and the direction in the circumference direction which are the same as the position and the direction in the circumference direction to the holding portion of CAM in the first cutting out a dental restoration. Therefore, it becomes possible to prepare a data in which a dental restoration to be cut out in the second cutting out is positioned in a proximity position proximate to a portion in which other dental restoration was cut out in the first cutting out the dental restoration.

That is, as shown in FIG. 3(B), because the mill blank for dental CAD/CAM of the present embodiment has the notched portion, it becomes possible to install the mill blank for dental CAD/CAM at the same position and the direction in the circumference direction when the mill blank for dental CAD/CAM is installed to CAM. Therefore, it becomes possible to minutely design and arrange the dental restoration to be prepared.

In contrast, in the conventional mill blank for dental CAD/CAM, as shown in FIG. 3(C), a relatively large interval must be provided between a dental restoration to be cut out in the second cutting out and a portion in which other dental restoration was cut out in the first cutting out the dental restoration. The reason is that it is necessary to prepare a cutting data of the dental restoration to be cut out in the second cutting out so that a dental restoration to be cut out in the second cutting out will not overlap with a portion in which other dental restoration was cut out in the first cutting out the dental restoration. This is because it is impossible to install the conventional mill blank for dental CAD/CAM at the same position and the direction in the circumference direction.

When the mill blank for dental CAD/CAM does not have the notched portion, the direction of installing in the circumference direction is not recognized. In contrast, because the mill blank for dental CAD/CAM of the present embodiment has the notched portion, it is possible to always install the mill blank for dental CAD/CAM to the holding portion of CAM at the same position and the same direction in the circumference direction. Therefore, it becomes possible to install the mill blank for dental CAD/CAM at the position and the direction which are the same as the position and the direction in the first installing the dental restoration to the holding portion of CAM. Further, by storing the first cutting data used for cutting the mill blank for dental CAD/CAM in the first cutting out, a part which is already cut may be clearly recognized. Therefore, a design of the cutting data of a dental restoration in a portion which is not cut is facilitated and the dental restoration may be easily prepared from the portion which is not cut.

In general, a dental restoration to be prepared is seldom arranged for cutting so as to form a large interval with respect to an adjacent dental restoration. In many cases, it is required to design and arrange a dental restoration to be prepared so as to form an interval of about 1 mm with respect to an adjacent dental restoration. In the present embodiment, it is possible to exactly match the position and the direction in the circumference direction of the mill blank for dental CAD/CAM in the cutting data of the dental restoration which is already cut out and the position and the direction in the circumference direction of the mill blank for dental CAD/CAM which is re-installed for further cutting out. Therefore, when installation of the mill blank for dental CAD/CAM to CAM and cutting is repeatedly performed, it is possible to prepare a cutting data in which more dental restorations than before are arranged in one mill blank for dental CAD/CAM. As a result, more dental restorations than before may be prepared from one mill blank for dental CAD/CAM.

Figure 4A:
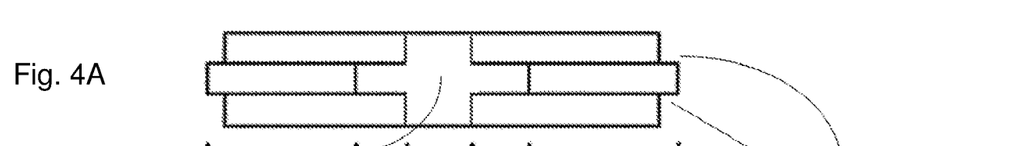
FIG. 4(A) is a side view of the mill blank for dental CAD/CAM of other embodiment of the present disclosure.

FIGS. 4(A) and (B) respectively show a side view and a plane view of a mill blank for dental CAD/CAM 1 of other embodiment of the present disclosure. Although the notched portion 3 in FIG. 2 is composed of a circular arc surface, a notched portion 3 of the present embodiment is composed of a plane surface. The mill blank for dental CAD/CAM 1 of the present embodiment has a notched portion 3 on a circumference portion 1a in addition to recesses 2 as compared with the mill blank for dental CAD/CAM shown in FIG. 1. In the present embodiment, a part of the recesses 2 is notched by the notched portion 3. Therefore, it is understood that the recesses 2 do not extend over the whole of the circumference portion of the mill blank for dental CAD/CAM 1.

Figure 4B:
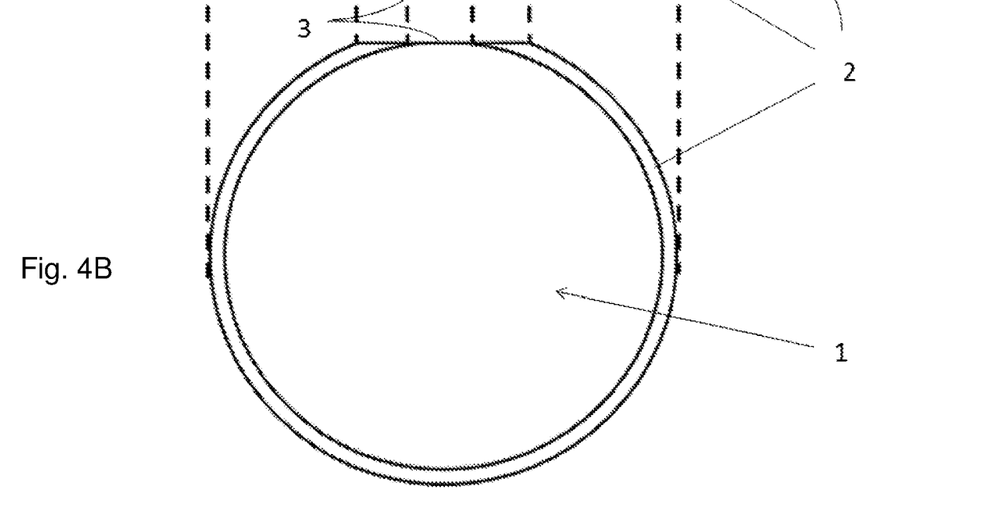
FIG. 4(B) is a plane view of the mill blank for dental CAD/CAM 1 of other embodiment of the present disclosure.

Because the mill blank for dental CAD/CAM 1 of the present embodiment has the notched portion 3, the direction of the mill blank for dental CAD/CAM in the circumference direction may be recognized. Therefore, when the mill blank for dental CAD/CAM is installed on a holding portion of CAM, there are no cases when the mill blank for dental CAD/CAM is installed in a wrong direction in the circumference direction. As a result, the mill blank for dental CAD/CAM of the present embodiment may be always installed at a constant position or a constant direction in the circumference direction.

In the present embodiment, the notched portion 3 is composed of a plane surface parallel to the center axis of the columnar shape of the mill blank for dental CAD/CAM 1. Further, the plane surface surface-contacts with the second surface 21b of the first recess 21 (and the second surface 22b of the second recess 22).

Figure 5A:
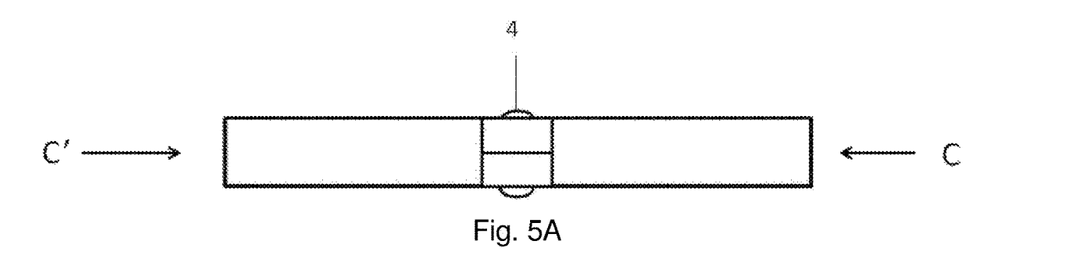
FIG. 5(A) is a side view of the holding portion of CAM.
Figure 5B:
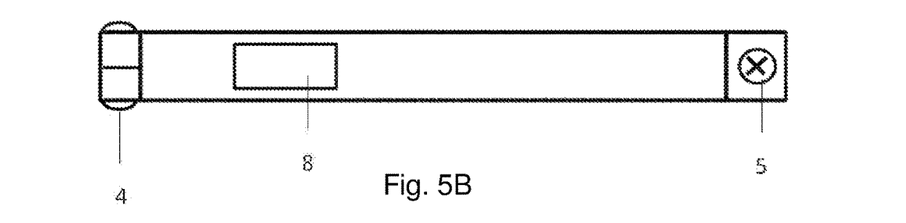
FIG. 5(B) is a side view of the holding portion of CAM viewed from a different direction from the direction of FIG. 5(A).
Figure 6A:
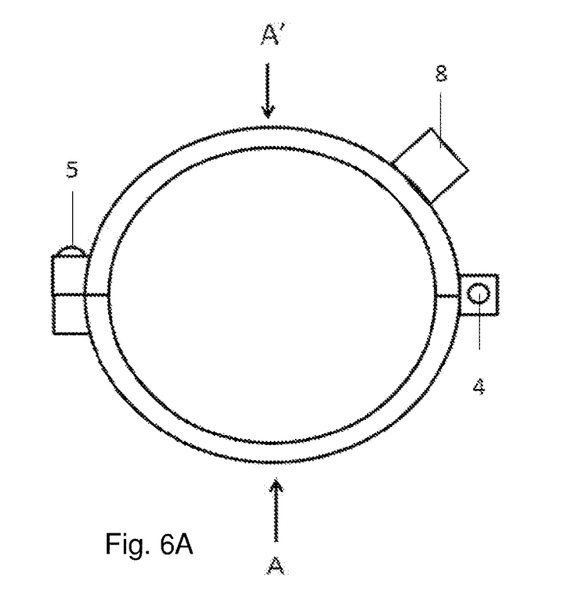
FIG. 6(A) is a plane view of the holding portion of CAM.
Figure 6B:
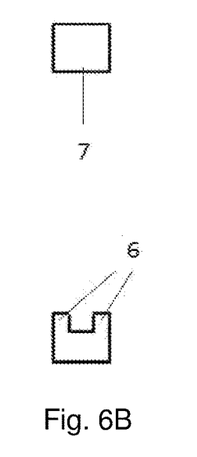
FIG. 6(B) is a sectional view taken along the line A-A' of FIG. 6(A).

FIG. 5(A) is a side view of a holding portion of CAM. FIG. 5(B) is a side view of a holding portion of CAM viewed from a different direction from the direction of FIG. 5(A). FIG. 6(A) is a plane view of the holding portion of CAM. FIG. 6(B) is a sectional view taken along the line A-A' of FIG. 6(A). In FIG. 6(B), sections are not hatched in order to facilitate understanding of components.

In the holding portion shown in FIG. 5, the mill blank for dental CAD/CAM is held by connecting one sides of two half cylindrical members by a hinge 4, closing other sides of two half cylindrical members so as to wrap the mill blank for dental CAD/CAM with a cylinder which is formed by two half cylindrical members and fastening other sides of two half cylindrical members with screw 5. The holding portion of CAM has an arm 8 jointing with CAM in order to connect to CAM.

As shown in FIG. 6(B) of the sectional view taken along the line A-A' of FIG. 6 (A), the holding portion has a positioning portion 7 which is fitted in the notched portion of the mill blank for dental CAD/CAM to position the mill blank for dental CAD/CAM. The positioning portion 7 may have various shapes according to the notched portion. The notched portion is formed by cut out parallel to the center axis of the columnar shape from the upper surface to the bottom surface of the mill blank for dental CAD/CAM. Therefore, the shape of the positioning portion 7 in the sectional view taken along the line A-A' of FIG. 6(A) is constant no matter what the positioning portion 7 has any shape. Further, a fitting portion 6 which fits in the recess of the mill blank for dental CAD/CAM is shown in FIG. 6(B). The mill blank for dental CAD/CAM is fixed by fitting the fitting portion 6 in the recess of the mill blank for dental CAD/CAM when the mill blank for dental CAD/CAM is installed. The fitting portion 6 is formed over the whole of the circumference without the positioning portion 7 which is fitted in the notched portion. In the present embodiment, by holding the mill blank for dental CAD/CAM over the whole of the circumference with the positioning portion 7 which is fitted in the notched portion and the fitting portion 6 which fits in the recess, it may be prevented that a breakage such as cracking and chipping and falling off from the holding portion occurs.

Figure 7:
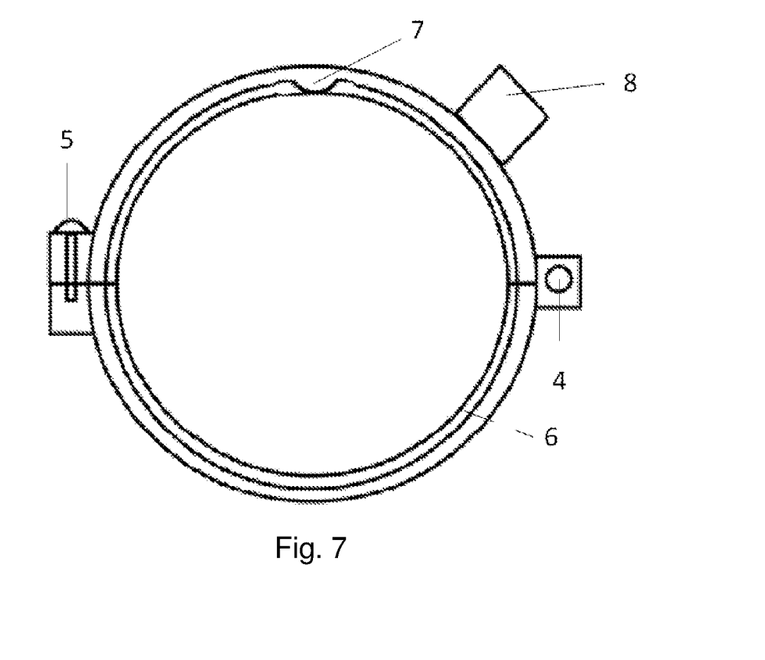
FIG. 7 is a sectional view of the holding portion of CAM of FIG. 5.

FIG. 7 is a sectional view taken along the line C-C' of the holding portion of CAM of FIG. 5. In FIG. 7, sections are not hatched in order to facilitate understanding of components. FIG. 7 is a sectional view taken at the center of the two fitting portions 6 shown in FIG. 6(A). The mill blank for dental CAD/CAM is held by connecting one sides of two half cylindrical members by a hinge 4, closing other sides of two half cylindrical members so as to wrap the mill blank for dental CAD/CAM with a cylinder which is formed by two half cylindrical members and fastening other sides of two half cylindrical members with screw 5. The holding portion of CAM of the present embodiment has an arm 8 jointing with CAM in order to connect to CAM. Because FIG. 7 is a sectional view, the shape of the positioning portion 7 which is fitted in the notched portion is shown in FIG. 7. In FIG. 7, the positioning portion 7 has a circular arc surface shape in order to engage to the mill blank for dental CAD/CAM shown in FIG. 2. It is preferable that the mill blank for dental CAD/CAM is held after engaging the notched portion 3 of the mill blank for dental CAD/CAM with the positioning portion 7 to fit the mill blank for dental CAD/CAM so as not to rotate in the circumference direction.

Figure 8:
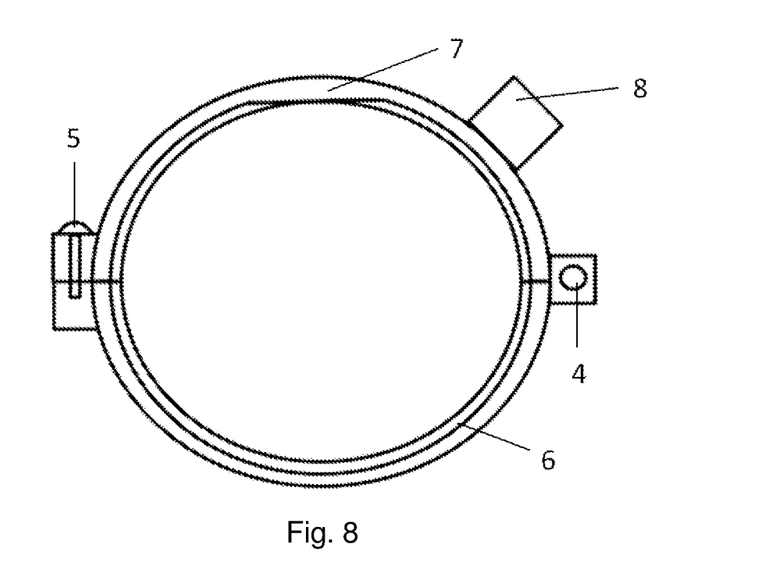
FIG. 8 is a variation of FIG. 7.

FIG. 8 is a variation of FIG. 7. In FIG. 8, sections are not hatched in order to facilitate understanding of components. In FIG. 8, the positioning portion 7 has a planar surface shape in order to engage to the mill blank for dental CAD/CAM shown in FIG. 4. It is preferable that the mill blank for dental CAD/CAM is held after engaging the notched portion 3 of the mill blank for dental CAD/CAM with the positioning portion 7 to fit the mill blank for dental CAD/CAM so as not to rotate in the circumference direction.

Figure 9A:
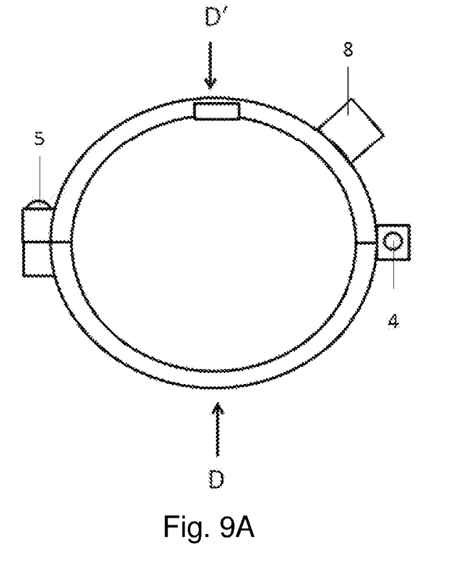
FIG. 9(A) is a plane view of the holding portion of CAM with the clip.
Figure 9B:
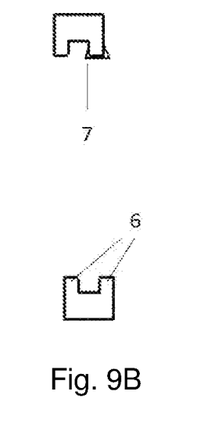
FIG. 9(B) is a sectional view taken along the line D-D' of FIG. 9(A).

FIG. 9(A) is a plane view of a holding portion of CAM with clip. FIG. 9(B) is a sectional view taken along the line D-D' of FIG. 9(A). In FIG. 9, sections are not hatched in order to facilitate understanding of components. In general, the holding portion of CAM is formed with a groove over the whole of the circumference for holding the recess of the mill blank for dental CAD/CAM. In FIG. 9(A), a portion provided with a clip fits with the notched portion to act as the positioning portion 7. It is preferable that a holding portion of CAM which is prepared for the present disclosure is used. The clip is used as an alternative to the positioning portion 7. However, because the clip is fall off to become unstable, it is preferable that the holding portion has the positioning portion 7 which is fitted in the notched portion.

In FIG. 9(B), the positioning portion 7 which is fitted in the notched portion is not shown in upper region. However, as shown in FIG. 9(A), the holding portion of CAM includes the clip as the positioning portion 7.

FIG. 10(A) to (D) show variations of the notched portion 3 respectively.

Figure 10:
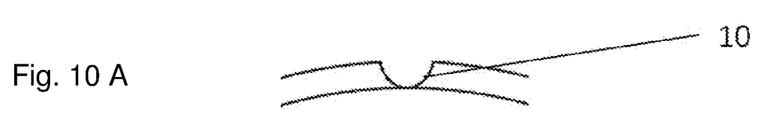
FIG. 10(A) is a variation of the notched portion.
FIG. 10(B) is a variation of the notched portion.
FIG. 10(C) is a variation of the notched portion.
FIG. 10(D) is a variation of the notched portion.

FIG. 10(A) shows an enlarged view of the notched portion 3 of the mill blank for dental CAD/CAM in the embodiment shown in FIG. 2. The notched portion 3 is composed of a circular arc surface 10.

Figure 10B:
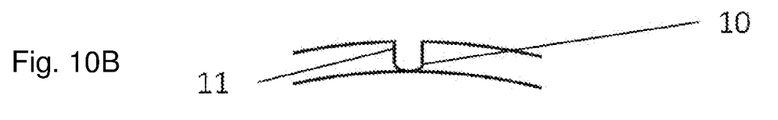

FIG. 10(B) shows an example of the notched portion composed of a plane surface and a curved surface. In FIG. 10(B), the notched portion consists of a pair of plane surfaces 11 extending in parallel with one another from the circumferential surface (side surface) of the mill blank for dental CAD/CAM and a circular arc surface which connects to both tips of the pair of plane surfaces and contacts with the recess.

Figure 10C:
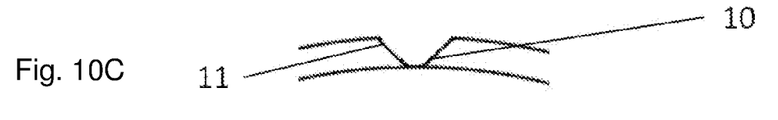

FIG. 10(C) shows other example of the notched portion composed of a plane surface and a curved surface. In FIG. 10(C), a pair of plane surfaces 11 does not extend in parallel with one another, and the distance between the pair of plane surfaces 11 spreads toward the circumferential surface (side surface) of the mill blank for dental CAD/CAM.

Figure 10D:
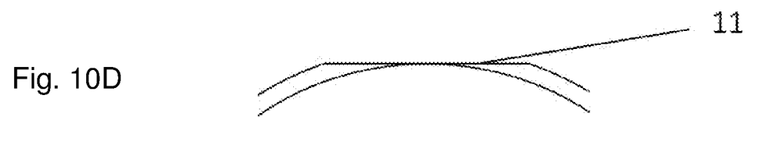

FIG. 10(D) shows an enlarged view of the notched portion of the mill blank for dental CAD/CAM of the embodiment shown in FIG. 4. The notched portion is composed of one plane surface 11.

Preferable notched portion has a shape shown in FIG. 10(A), FIG. 10(B) or FIG. 10(C).

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

A mill blank for dental CAD/CAM of the present disclosure may be specifically used for a disk for preparing a dental restoration by cutting and machining using CAD/CAM technique.

What is claimed is:

1. A mill blank for dental CAD/CAM for preparing a dental restoration by being installed in a CAD/CAM device, wherein,
   the mill blank for dental CAD/CAM has a columnar shape,
   the mill blank for dental CAD/CAM has at least two recesses which includes a first recess opening to an upper surface of the mill blank for dental CAD/CAM and a second recess opening to a bottom surface of the mill blank for dental CAD/CAM, and a circumference portion separating the first recess and the second recess, wherein the circumference portion contains only one notched portion for installing the mill blank for dental CAD/CAM in the same direction,
   the first recess and the second recess respectively include a first surface which is parallel to the upper surface and the bottom surface and a second surface which is a circumferential surface concentric with the circumferential surface of the mill blank for dental CAD/CAM and is vertical to the first surface,
   the notched portion is composed of a plane surface and a circular arc surface which are parallel to the center axis of the columnar shape of the mill blank for dental CAD/CAM and contacts with the second surface,
   a portion of the notched portion contacting with the second surface of the recess is the circular arc surface.

2. The mill blank for dental CAD/CAM of claim 1, wherein,
   a diameter of the columnar shape of the mill blank for dental CAD/CAM is within a range of 95 to 100 mm, and a height of the columnar shape of the mill blank for dental CAD/CAM is within a range of 10 to 35 mm.

3. The mill blank for dental CAD/CAM of claim 2, wherein,
   the diameter of the columnar shape of the mill blank for dental CAD/CAM is 98 mm, and the height of the columnar shape of the mill blank for dental CAD/CAM is 14, 18 or 26 mm.

4. The mill blank for dental CAD/CAM of claim 3, wherein,
   a distance between the first recess and the second recess in the axial direction of the columnar shape of the mill blank for dental CAD/CAM is 10 mm.

5. The mill blank for dental CAD/CAM of claim 4, wherein,
   a dimension from the center axis of the columnar shape of the mill blank for dental CAD/CAM to the first recess and the second recess is 94 mm.

6. The mill blank for dental CAD/CAM of claim 2, wherein,
   a distance between the first recess and the second recess in the axial direction of the columnar shape of the mill blank for dental CAD/CAM is within a range of 9 to 11 mm.

7. The mill blank for dental CAD/CAM of claim 6, wherein,
   a dimension from the center axis of the columnar shape of the mill blank for dental CAD/CAM to the first recess and the second recess is within a range of 90 to 98 mm.

8. The mill blank for dental CAD/CAM of claim 1, wherein,
   the mill blank for dental CAD/CAM has only two recesses.

9. The mill blank for dental CAD/CAM of claim 1, wherein the mill blank for dental CAD/CAM consists of a ceramic material which is unsintered or is not subjected to final sintering.

10. The mill blank for dental CAD/CAM of claim 9, wherein the ceramic material contains alumina or zirconia at a ratio of 95 wt. % or more.

11. The mill blank for dental CAD/CAM of claim 9, wherein a primary average particle diameter of the ceramic material is within the range of 0.01 to 10 μm.

12. A set including the mill blank for dental CAD/CAM of claim 1 and a holding portion of a CAM which cuts out the mill blank for dental CAD/CAM, wherein,
    the holding portion of the CAM includes an engaging portion which engages to a whole of the recess of the mill blank for dental CAD/CAM,
    the mill blank for dental CAD/CAM is held at the engaging portion, and
    the holding portion further includes a positioning portion which fits in the notched portion of the mill blank for dental CAD/CAM.

* * * * *